US012708345B2

(12) United States Patent
Wang et al.

(10) Patent No.: US 12,708,345 B2
(45) Date of Patent: Aug. 18, 2026

(54) ULTRASOUND IMAGING METHOD, ULTRASOUND IMAGING SYSTEM, AND NON-TRANSITORY COMPUTER-READABLE MEDIUM

(71) Applicant: GE Precision Healthcare LLC, Waukesha, WI (US)

(72) Inventors: Zhiwen Wang, Wuxi (CN); Minyu Gu, Wuxi (CN); Gang Liu, Wuxi (CN); Ke Tao, Wuxi (CN)

(73) Assignee: Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/757,067

(22) Filed: Jun. 27, 2024

(65) Prior Publication Data

US 2025/0000484 A1 Jan. 2, 2025

(30) Foreign Application Priority Data

Jun. 30, 2023 (CN) ......................... 202310797944.5

(51) Int. Cl.
*A61B 8/14* (2006.01)
*A61B 8/00* (2006.01)

(52) U.S. Cl.
CPC .............. *A61B 8/14* (2013.01); *A61B 8/4272* (2013.01); *A61B 8/4477* (2013.01); *A61B 8/461* (2013.01)

(58) Field of Classification Search
CPC ....... A61B 8/14; A61B 8/4272; A61B 8/4477; A61B 8/461; A61B 2017/3413; A61B 8/0841; A61B 8/085; A61B 8/4245; A61B 8/483; A61B 8/44; A61B 8/4488; A61B 8/469; A61B 17/3403; G06V 10/25; G06V 10/422; G06V 10/764; G06V 10/82; G06V 2201/03
See application file for complete search history.

(56) References Cited

U.S. PATENT DOCUMENTS

2010/0113929 A1* 5/2010 Yeh .......................... A61B 8/08 600/443
2013/0245427 A1* 9/2013 Rothgang .......... A61B 17/3403 600/411
2018/0353156 A1* 12/2018 Mehanian ............ A61B 8/4444
2019/0142528 A1* 5/2019 Vertikov ............ A61B 1/00172 600/424
2020/0015785 A1* 1/2020 Attia ...................... A61B 8/466
2024/0260934 A1* 8/2024 De Craene ........... A61B 8/4263

* cited by examiner

*Primary Examiner* — Alexei Bykhovski

(57) ABSTRACT

An ultrasound imaging method, including: receiving, by using a probe, an ultrasonic echo signal from a tissue to be imaged; processing the ultrasonic echo signal to generate a volumetric ultrasound image of the tissue to be imaged; identifying a tissue to be subjected to intervention in the volumetric ultrasound image; and generating a movement guide for the probe based on image information of the identified tissue to be subjected to intervention, and displaying the same.

17 Claims, 6 Drawing Sheets

ULTRASOUND IMAGING METHOD, ULTRASOUND IMAGING SYSTEM, AND NON-TRANSITORY COMPUTER-READABLE MEDIUM

CROSS-REFERENCE TO RELATED APPLICATION

This application claim priority to Chinese Patent Application No. 202310797944.5, which was file on Jun. 30, 2023 at the Chinese Patent Office. The entire contents of the above-listed application are incorporated by reference herein in their entirety.

TECHNICAL FIELD

The present invention relates to the field of ultrasound imaging and, in particular, to an ultrasound imaging method, an ultrasound imaging system, and a non-transitory computer-readable medium.

BACKGROUND

Ultrasonic imaging technology is a real-time, lossless imaging technology that utilizes a probe to receive an ultrasonic echo signal from a site to be imaged, and then processes the ultrasonic echo signal to perform imaging. In some application scenarios, ultrasonic imaging can assist in the determination of the position of a lesion in an interventional operation in real time, thereby helping physicians to perform an operation such as a biopsy or removal of the lesion, or the like.

Due to large differences in information such as the size, morphology, and location of lesions in different individuals, physicians typically need to perform extensive observation and analysis on a lesion, and finally determine an optimal surgical plan before performing an interventional operation. The described process consumes a great amount of time and effort. In addition, during an interventional operation, a physician needs to pay attention to an interventional object on the one hand, and on the other hand, needs to constantly observe an ultrasound image to adjust an ultrasonic probe, and this procedure also imposes a burden on the physician.

SUMMARY

Some embodiments of the present application provide an ultrasound imaging method, comprising: receiving, by using a probe, an ultrasonic echo signal from a tissue to be imaged; processing the ultrasonic echo signal to generate a volumetric ultrasound image of the tissue to be imaged; identifying a tissue to be subjected to intervention in the volumetric ultrasound image; and generating a movement guide for the probe on the basis of image information of the identified tissue to be subjected to intervention, and displaying the same.

Some embodiments of the present application provide an ultrasound imaging system, comprising: a probe; a processor; and a display apparatus, used to receive a signal from the processor and perform a display operation. The processor is configured to perform the following method: receiving, by using a probe, an ultrasonic echo signal from a tissue to be imaged; processing the ultrasonic echo signal to generate a volumetric ultrasound image of the tissue to be imaged; identifying a tissue to be subjected to intervention in the volumetric ultrasound image; and generating a movement guide for the probe on the basis of image information of the identified tissue to be subjected to intervention, and displaying the same.

Some embodiments of the present application provide a non-transitory computer-readable medium, the non-transitory computer-readable medium storing a computer program having at least one code segment that is executable by a machine to perform the following method steps: receiving, by using a probe, an ultrasonic echo signal from a tissue to be imaged; processing the ultrasonic echo signal to generate a volumetric ultrasound image of the tissue to be imaged; identifying a tissue to be subjected to intervention in the volumetric ultrasound image; and generating a movement guide for the probe on the basis of image information of the identified tissue to be subjected to intervention, and displaying the same.

It should be understood that the brief description above is provided to introduce, in a simplified form, concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any deficiencies raised above or in any section of the present disclosure.

BRIEF DESCRIPTION OF THE DRAWINGS

The present application will be better understood by reading the following description of non-limiting embodiments with reference to the accompanying drawings, where.

DETAILED DESCRIPTION

Specific embodiments of the present invention will be described below. It should be noted that in the specific description of the embodiments, it is impossible to describe all features of the actual embodiments of the present invention in detail, for the sake of brief description. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless otherwise defined, the technical or scientific terms used in the claims and the description should be as they are usually understood by those possessing ordinary skill in the technical field to which they belong. "First", "second", and similar words used in the present invention and the claims do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
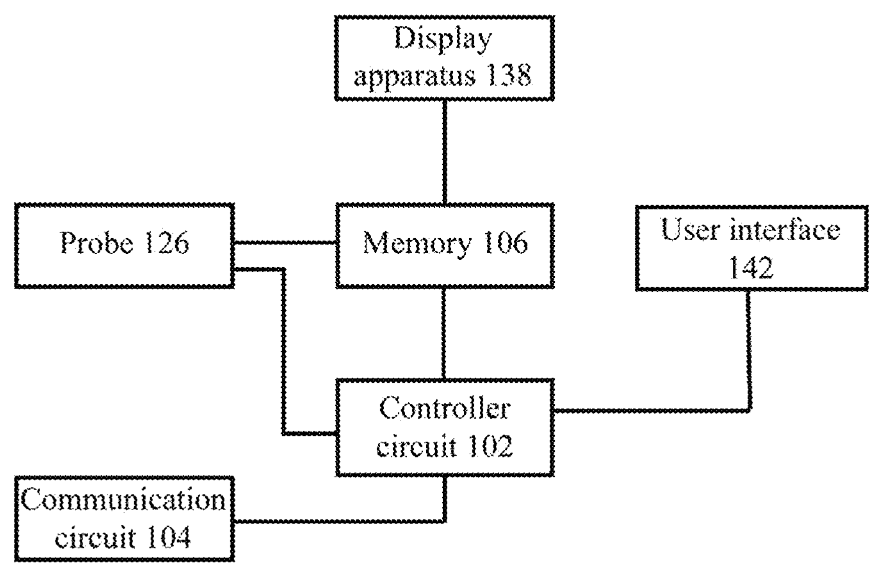
FIG. 1 is a schematic diagram of an ultrasound imaging system according to some embodiments of the present application.

FIG. 1 shows a schematic block diagram of an embodiment of an ultrasound imaging system 100. The ultrasound imaging system 100 may include a controller circuit 102, a display apparatus 138, a user interface 142, a probe 126, and a memory 106, which can be operatively connected to a communication circuit 104.

The controller circuit 102 is configured to control operation of the ultrasonic imaging system 100. The controller circuit 102 may comprise one or more processors. Optionally, the controller circuit 102 may comprise a central processing unit (CPU), one or more microprocessors, a graphics processing unit (GPU), or any other electronic component capable of processing inputted data according to a specific logic instruction. Optionally, the controller circuit 102 may comprise and/or represent one or more hardware circuits or circuit systems, and the hardware circuit or circuit system comprises, is connected to, or comprises and is connected to one or more processors, controllers, and/or other hardware logic-based apparatuses. Additionally or alternatively, the controller circuit 102 may execute an instruction stored on a tangible and non-transitory computer-readable medium (e.g., the memory 106).

The controller circuit 102 may be operatively connected to and/or control the communication circuit 104. The communication circuit 104 is configured to receive and/or transmit information along a bidirectional communication link with one or more alternate ultrasound imaging systems, remote servers, etc. The remote server may represent patient information, a machine learning algorithm, a remotely stored medical image from a previous scan, and/or a diagnosis and treatment period of a patient, etc. The communication circuit 104 may represent hardware for transmitting and/or receiving data along a bidirectional communication link. The communication circuit 104 may include a transceiver, a receiver, etc., and an associated circuit system (e.g., an antenna) for communicating (e.g., transmitting and/or receiving) with the one or more alternate ultrasound imaging systems, remote servers, etc., by using a wired and/or wireless means. For example, protocol firmware for transmitting and/or receiving data along a bidirectional communication link may be stored in the memory 106 accessed by the controller circuit 102. The protocol firmware provides network protocol syntax to the controller circuit 102 so as to assemble a data packet, establish and/or segment data received along the bidirectional communication link, and so on.

The bidirectional communication link may be a wired (e.g., by means of a physical conductor) and/or wireless communication (e.g., utilizing a radio frequency (RF)) link for exchanging data (e.g., a data packet) between the one or more alternative ultrasound imaging systems, remote servers, etc. The bidirectional communication link may be based on a standard communication protocol, such as Ethernet, TCP/IP, Wi-Fi, 802.11, a customized communication protocol, Bluetooth, etc.

The controller circuit 102 is operatively connected to the display apparatus 138 and the user interface 142. The display apparatus 138 may include one or more liquid crystal display apparatuses (e.g., light emitting diode (LED) backlights), organic light emitting diode (OLED) display apparatuses, plasma display apparatuses, CRT display apparatuses, and the like. The display apparatus 138 may display patient information, one or more medical images and/or videos, a graphical user interface, or a component received by the display device 138 from the controller circuit 102, one or more 2D, 3D, or 4D ultrasonic image data sets from ultrasonic data stored in the memory 106, or an anatomical measurement, a diagnosis, processing information, and the like currently acquired in real time.

The user interface 142 controls the operation of the controller circuit 102 and the ultrasonic imaging system 100. The user interface 142 is configured to receive an input from a clinician and/or an operator of the ultrasonic imaging system 100. The user interface 142 may include a keyboard, a mouse, a trackball, a touch pad, one or more physical buttons, and the like. Optionally, the display apparatus 138 may be a touch screen display apparatus that includes at least a portion of the user interface 142. For example, a portion of the user interface 142 may correspond to a graphical user interface (GUI) that is generated by the controller circuit 102 and is shown on the display apparatus 138. The touch screen display apparatus may detect the presence of a touch from the operator on the display apparatus 138, and may also identify the location of the touch relative to the surface area of the display apparatus 138. For example, a user may select, by touching or contacting the display apparatus 138, one or more user interface components of the user interface (GUI) shown on the display device. User interface components may correspond to icons, text boxes, menu bars, etc., shown on the display apparatus 138. A clinician may select, control, and use a user interface assembly, interact with the same, and so on, so as to send an instruction to the controller circuit 102 to perform one or more operations described in the present application. For example, a touch may be applied using at least one among a hand, a glove, a stylus, and the like.

The memory 106 includes a parameter, an algorithm, one or more protocols of ultrasound examination, data values, and the like used by the controller circuit 102 to execute one or more operations described in the present application. The memory 106 may be a tangible and non-transitory computer-readable medium such as a flash memory, a RAM, a ROM, an EEPROM, etc. The memory 106 may include one or more learning algorithms (e.g., deep learning algorithms including a convolutional neural network algorithm, machine learning algorithms such as a decision tree learning algorithm, a conventional computer vision algorithm, or the like) configured to define an image analysis algorithm. During execution of the image analysis algorithm, the controller circuit 102 is configured to identify a section (or a view or an anatomical plane) of an anatomical structure of interest in a medical image. Optionally, an image analysis algorithm may be received by means of the communication circuit 104 along one among bidirectional communication links, and stored in the memory 106. It can be understood that the anatomical structure of interest may be a specific anatomical feature in a site to be scanned, and may be, for example, a muscle, a blood vessel, a tissue to be subjected to intervention (e.g., a tumor), etc.

The image analysis algorithm may be defined by one or more algorithms to identify a section of a subject to be scanned of interest based on one or more anatomical features within the medical image (e.g., a boundary, thickness, pixel value change, valve, cavity, chamber, edge or inner layer, vessel structure, etc.), a modality or pattern of the medical image (e.g., color blood flow), etc. The one or more anatomical features may represent a feature of pixels and/or voxels of the medical image, such as a histogram of oriented gradients, a point feature, a covariance feature, a binary mode feature, and the like. For example, the image analysis algorithm may be defined by using prediction of object identification within the medical image by using one or more deep neural networks.

The image analysis algorithm may correspond to an artificial neural network formed by the controller circuit 102 and/or the remote server. The image analysis algorithm may be divided into two or more layers, such as an input layer for receiving an input image, an output layer for outputting an output image, and/or one or more intermediate layers. Layers of a neural network represent different groups or sets of artificial neurons, and may represent different functions that are executed by the controller circuit 102 with respect to an input image (e.g., an ultrasonic image acquired and/or generated by the ultrasonic imaging system 100) to identify an object of the input image and determine a section of an anatomical structure of interest shown in the input image. An artificial neuron in a layer of the neural network may examine an individual pixel in the input image. The artificial neurons use different weights in a function applied to the input image, so as to attempt to identify an object in the input image. The neural network produces an output image by assigning or associating different pixels in the output image with different anatomical features on the basis of the analysis of pixel characteristics.

The image analysis algorithm is defined by a plurality of training images. For a 2D image, the plurality of training images may be grouped into different anatomical planes of interest of the anatomical structure of interest. The training images may represent different orientations and/or cross sections of the anatomical structure of interest corresponding to different fields of view. For a 4D image, the plurality of training images may be grouped into volumetric images of the whole or part of the anatomical structure of interest. The training images may represent different orientations and/or outer contours of the anatomical structure of interest corresponding to different fields of view in a space. Additionally or alternatively, the image analysis algorithm may be defined by the controller circuit on the basis of a classification model. The classification model may correspond to a machine learning algorithm based on a classifier (e.g., a random forest classifier, principal component analysis, etc.) configured to identify and/or assign anatomical features to multiple types or categories based on overall shape, spatial position relative to the anatomical structure of interest, intensity, etc.

The controller circuit 102 executing an image analysis algorithm (e.g., an image analysis algorithm) may determine, based on the relationship of the anatomical features relative to each other, modality, etc., a section/outer contour corresponding to a current ultrasonic image.

Additionally or alternatively, the controller circuit 102 may define a separate image analysis algorithm customized and/or configured for different selected anatomical structures of interest. For example, a plurality of image analysis algorithms may be stored in the memory 106. Each algorithm among the plurality of image analysis algorithms may be customized and/or configured on the basis of different training images (e.g., a set of input images) to configure layers of different neural networks, so as to select anatomical structures of interest, classification models, supervised learning models, and the like.

With further reference to FIG. 1, the ultrasound imaging system 100 may include a probe 126. The probe 126 has elements such as an ultrasonic transducer, a transmitter, a transmit beam former, a detector/SAP electronics, etc., (not shown). The detector/SAP electronics may be used to control the switching of the transducer elements. The detector/SAP electronics may also be used to group the transducer elements into one or more sub-holes. Configurations of the probe 126 will also be described below exemplarily. The probe 126 may be any type of probe, including a linear probe, a curved array probe, a 1.25D array probe, a 1.5D array probe, a 1.75D array probe, or a 2D array probe. According to a preferred embodiment of the present application, the probe 126 may be a probe for volumetric imaging. For example, the probe 126 may be an electronic 4D (E4D) probe. In addition, the probe 126 may also be a mechanical probe, for example, a mechanical 4D probe or a hybrid probe. The probe 126 may be configured to acquire 4D ultrasound data, and the 4D ultrasound data includes information about how the volume changes over time, and may be processed to obtain a volumetric ultrasound image related to the site to be imaged. It can be understood that each volume may include a plurality of 2D images or slices, and accordingly, the controller circuit may select a required 2D image from the volumetric ultrasound images.

The probe 126 may be configured to acquire ultrasound data or information from tissue to be imaged (e.g., organs such as breasts and the heart, corresponding skin surfaces outside organs, etc.) of a patient. The probe 126 is communicatively connected to the controller circuit by means of the transmitter. The transmitter transmits a signal to the transmit beam former on the basis of acquisition settings received by the controller circuit 102. The acquisition settings may define the amplitude, pulse width, frequency, gain setting, scanning angle, power, time gain compensation (TGC), resolution, and the like of the ultrasonic pulses emitted by the ultrasonic transducer. The ultrasonic transducer emits a pulsed ultrasonic signal into a patient (e.g., the body). The acquisition settings may be defined by a user operating the user interface 142. The signal transmitted by the transmitter, in turn, drives the ultrasonic transducer.

The ultrasonic transducer transmits the pulsed ultrasonic signal to a body (e.g., a patient) or a volume that corresponds to an acquisition setting along one or more scanning planes. The ultrasonic signal may include, for example, one or more reference pulses, one or more push pulses (e.g., shear waves), and/or one or more pulsed wave Doppler pulses. At least a portion of the pulsed ultrasonic signal is backscattered from a tissue to be imaged (e.g., an organ, bone, heart, breast tissue, liver tissue, cardiac tissue, prostate tissue, newborn brain, embryo, abdomen, etc.) to produce an echo. Depending on the depth or movement, the echo is delayed in time and/or frequency, and received by the ultrasonic transducer. The ultrasonic signal may be used for imaging, for producing and/or tracking a shear wave, for measuring changes in location or velocity within the anatomical structure and a compressive displacement difference (e.g., strain) of tissue, and/or for treatment and other applications. For example, the probe 126 may deliver low energy pulses during imaging and tracking, deliver medium and high energy pulses to produce shear waves, and deliver high energy pulses during treatment.

The ultrasonic transducer converts a received echo signal into an electrical signal that can be received by the receiver. The receiver may include one or more amplifiers, analog/digital converters (ADCs), and the like. The receiver may be configured to amplify the received echo signal after appropriate gain compensation, and convert these analog signals received from each transducer element into a digitized signal that is temporally uniformly sampled. The digitized signals representing the received echoes are temporarily stored in the memory 106. The digitized signals correspond to the backscattered waves received by each transducer element at different times. After being digitized, the signal may still retain the amplitude, frequency, and phase information of the backscattered wave.

Optionally, the controller circuit 102 may retrieve the digitized signals stored in the memory 106 for use in a beam former processor. For example, the controller circuit 102 may convert the digitized signal into a baseband signal or compress the digitized signal.

In some embodiments, the controller circuit 102 may further include a beam forming processor. The beam forming processor may include one or more processors. If desired, the beam forming processor may include a central processing unit (CPU), one or more microprocessors, or any other electronic component capable of processing the input data according to specific logic instructions. Additionally or alternatively, the beam forming processor may execute instructions stored on a tangible and non-transitory computer-readable medium (e.g., the memory 106) to perform beam forming computation using any suitable beam forming method, such as adaptive beam forming, synthetic emission focusing, aberration correction, synthetic aperture, clutter suppression, and/or adaptive noise control, etc.

In some embodiments, the controller circuit 102 may further include a radio frequency (RF) processor. The beam forming processor executes beam forming on the digitized signals of the transducer elements, and outputs an RF signal. The RF signal is then provided to the RF processor for processing the RF signal. The RF processor may include one or more processors. If desired, the RF processor may include a central processing unit (CPU), one or more microprocessors, or any other electronic component capable of processing the inputted data according to specific logic instructions. Additionally or alternatively, the RF processor may execute instructions stored on a tangible and non-transitory computer-readable medium (e.g., the memory 106). Optionally, the RF processor may be integrated with and/or be part of the controller circuit 102. For example, operations described as being executed by the RF processor may be configured to be executed by the controller circuit 102.

The RF processor may generate, for a plurality of scanning planes or different scanning modes, different ultrasonic image data types and/or modes, e.g., B-mode, color Doppler (e.g., color blood flow, velocity/power/variance), tissue Doppler (velocity), and Doppler energy, on the basis of a predetermined setting of a first model. For example, the RF processor may generate tissue Doppler data for multiple scanning planes. The RF processor acquires the information (e.g., I/Q, B-mode, color Doppler, tissue Doppler, and Doppler energy information) related to a plurality of data pieces, and stores the data information in the memory 106, where the data information may include time stamp and orientation/rotation information.

Optionally, the RF processor may include a composite demodulator (not shown) for demodulating the RF signal to generate an IQ data pair representing an echo signal. The RF or IQ signal data may be provided directly to the memory 106 so as to be stored (e.g., stored temporarily). If desired, an output of the beam forming processor may be delivered directly to the controller circuit 102.

The controller circuit 102 may be configured to process the acquired ultrasonic data (e.g., RF signal data or an IQ data pair), and prepare and/or generate an ultrasound image data frame representing an anatomical structure of interest so as to display the same on the display apparatus 138. The acquired ultrasonic data may be processed by the controller circuit 102 in real time when an echo signal is received in a scanning or treatment process of ultrasound examination. Additionally or alternatively, the ultrasonic data may be temporarily stored in the memory 106 in a scanning process, and processed in a less real-time manner in live or off-line operations.

The memory 106 may be used to store processed frames of acquired ultrasound data that are not scheduled to be immediately displayed, or may be used to store post-processed images (e.g., shear wave images and strain images), firmware or software corresponding to, for example, a graphical user interface, one or more default image display settings, programmed instructions, and the like. The memory 106 may store medical images, such as a volumetric ultrasound image data set of ultrasound data, where such a volumetric ultrasound image data set is accessed to present two-dimensional and volumetric images. For example, the volumetric ultrasound image data set may be mapped to the corresponding memory 106 and one or more reference planes. Processing of ultrasound data that includes the ultrasound image data set may be based in part on user input, e.g., a user selection received at the user interface 142.

In some embodiments, the ultrasound imaging system 100 described above may be used to assist a physician in performing an interventional operation. As set forth above in the present application, in existing ultrasound-guided interventional operations, physicians typically perform two-dimensional ultrasound imaging by using an ultrasonic probe to determine the position of the tissue to be subjected to intervention (e.g., a tumor or other lesions) and to track an interventional object. In the above procedure, on the one hand, attention needs to pay to whether the interventional object is correctly positioned relative to the tissue to be subjected to intervention, and on the other hand, the position of the ultrasonic probe needs to be adjusted to ensure a good imaging effect. Therefore, the entire procedure requires a great deal of labor, and imposes high requirements on the operating skills of the physician. To address at least the technical problems described above, improvements are provided in embodiments of the present application. An exemplary description is provided below.

Figure 2:
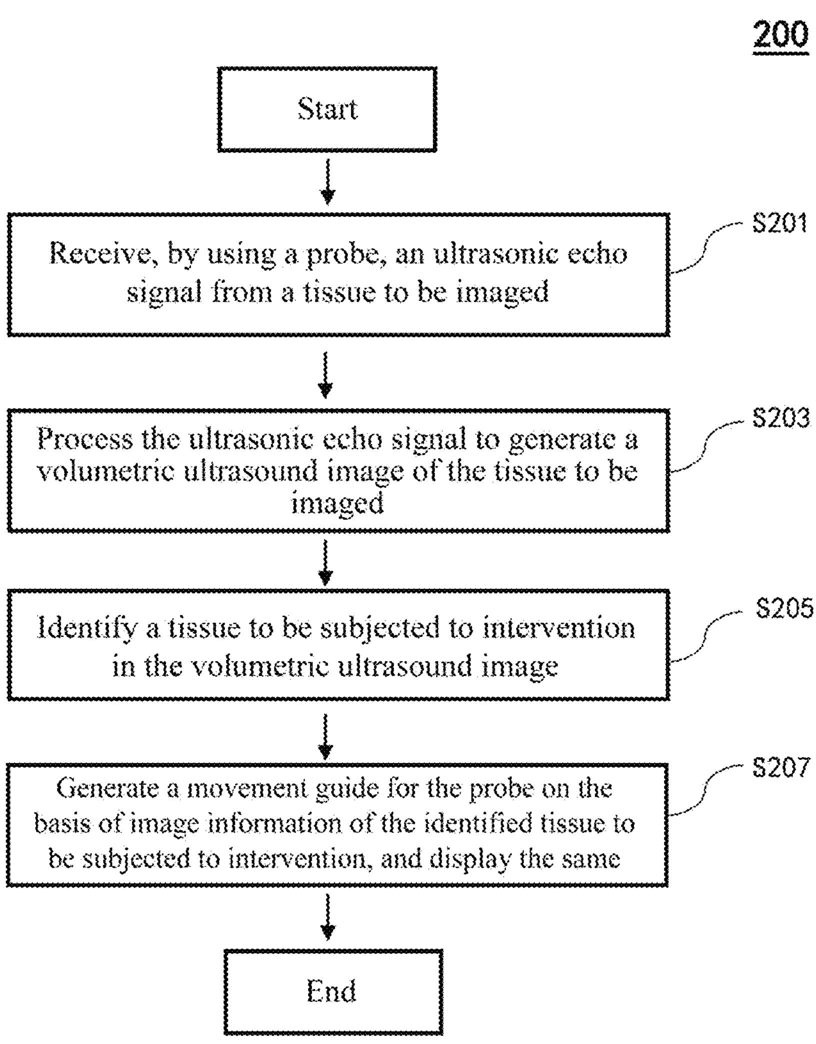
FIG. 2 is a schematic diagram of an ultrasound imaging method according to some embodiments of the present application.

Referring to FIG. 2, FIG. 2 shows a schematic diagram of an ultrasonic imaging method 200 according to some embodiments of the present application. The method 200 can be implemented by the ultrasound imaging system disclosed in any embodiment herein.

In step 201, an ultrasonic echo signal from a tissue to be imaged is received by using a probe. The step may be implemented by a processor, and for example, may be implemented by a processor of the controller circuit 102 in the ultrasound imaging system 100. Specifically, the ultrasonic probe may be controlled by the processor to emit an ultrasound signal to the tissue to be imaged, and the ultrasonic echo signal of the tissue to be imaged can be received by the probe and subsequently processed by the processor. The probe is a probe capable of volumetric ultrasound imaging. For example, the probe may be the E4D probe or the mechanical 4D probe set forth above in the present application. The specific type of the tissue to be imaged may be arbitrary, and may be, for example, a breast, a muscle, another human organ, or the like. In some of the following examples, a breast is used as an example for illustrative purposes, but not as a limitation.

In step 203, the ultrasonic echo signal is processed to generate a volumetric ultrasound image of the tissue to be imaged. Upon receiving the ultrasonic echo signal from the tissue to be imaged, the processor may perform, by means of processing the echo signal, real-time volumetric ultrasound imaging on the tissue to be imaged. The volumetric ultrasound imaging can obtain three-dimensional information about the interior of the tissue to be imaged. The information is, for example, information about an anatomical feature such as an organ inside the tissue to be imaged, information about a lesion, and the like.

In step 205, a tissue to be subjected to intervention is identified in the volumetric ultrasound image. In some examples, image recognition may be performed the volumetric ultrasound image described above by the processor. A specific image recognition method may be performed by an artificial intelligence means, or may be performed by any other means in the art, such as a threshold algorithm, which has been exemplarily described above and will not be further described herein. Furthermore, the processor may also directly process a volumetric ultrasound signal obtained in step 201 to identify the tissue to be subjected to intervention. The tissue to be subjected to intervention may be a specific lesion, for example, a tumor or the like.

In step 207, a movement guide for the probe is generated on the basis of image information of the identified tissue to be subjected to intervention, and the same is displayed. Upon identifying the tissue to be subjected to intervention, the processor may analyze the tissue to be subjected to intervention in the volumetric image to obtain other image information thereof. Further, the processor can automatically determine a preferred probe position (or a target probe position) according to the image information of the tissue to be subjected to intervention, generate the movement guide for the probe according to the difference between a current probe position and the target probe position, and display the same. It can be understood that the above-described target probe position may be a probe position that is determined by the processor after analyzing current image information of the tissue to be subjected to intervention and is more advantageous for imaging of the tissue to be subjected to intervention.

The configurations in the above embodiment can ensure that a physician imaging the interior of the tissue to be imaged finds the relative position of the tissue to be subjected to intervention more quickly and accurately. The reason is that a volumetric ultrasound image can provide more image information in a larger range than two-dimensional ultrasound images widely used in interventional operations. Accordingly, the tissue to be subjected to intervention is more easily detected by the probe. In addition, in the above embodiment, the movement guide for the probe is further automatically generated according to the identified image information to be subjected to intervention, so as to guide the physician to place the probe at the target position, thereby facilitating improvement in ultrasonic scanning and the efficiency of the interventional operation. Especially for a less experienced physician, the display of the movement guide greatly improves scanning efficiency.

In some examples, the volumetric ultrasound image and the image of the interventional object are configured to be displayed on the display apparatus along with the movement guide for the probe. In this way, the physician can experience changes in the image more intuitively during the movement of the probe, especially changes in the interventional object in the field of view. In a further embodiment, the volumetric ultrasound image and the image of the interventional object may be configured not to be displayed, and instead, only the movement guide for the probe is displayed.

The image information of the tissue to be subjected to intervention may include a plurality of types. In an example, the above-described image information may include size information of the tissue to be subjected to intervention. For example, the image information may include the specific morphology of an outer contour of the tissue to be subjected to intervention, the length direction of the greatest length and the width direction of the greatest width of the tissue to be subjected to intervention, etc. In some scenarios, such information affects planning performed by the physician for a path of the intervention. For example, performing an interventional operation in the length direction generally facilitates better sampling or lesion removal. Acquisition of the above-described size information facilitates planning performed by the processor for the movement guide for the probe. In another example, the above-described image information may include orientation information of the tissue to be subjected to intervention in the volumetric ultrasound image. For example, the image information may include the position of the tissue to be subjected to intervention in the field of view of the volumetric ultrasound image, and the orientation of the tissue to be subjected to intervention in the field of view of the volumetric ultrasound image. In some scenarios, placing the tissue to be subjected to intervention in the center of the field of view and aligning the field of view with the tissue to be subjected to intervention are more advantageous for an intervention operation. Furthermore, in other examples, the above-described image information may also include the size information of the tissue to be subjected to intervention and the orientation information of the tissue to be subjected to intervention in the volumetric ultrasound image.

Further, the above-described movement guide may be configured to: guide the probe to move so that the tissue to be subjected to intervention is substantially located in a middle position of the volumetric ultrasound image and the length direction of the tissue to be subjected to intervention is substantially parallel to a lateral plane of the volumetric ultrasound image.

Such configurations can ensure that the tissue to be subjected to intervention is in an optimal imaging position, thereby providing better conditions for a subsequent interventional imaging procedure. For example, the tissue to be subjected to intervention is substantially located in the middle position of the volumetric ultrasound image, so that it can be ensured that during subsequent imaging, both the interventional object and the tissue to be subjected to intervention can be completely and clearly exposed within the range of the field of view of the ultrasound image, thereby facilitating imaging performed on the interventional object and the tissue to be subjected to intervention during the entire interventional procedure. The length direction of the tissue to be subjected to intervention is substantially parallel to the lateral plane of the volumetric ultrasound image, so that it can be ensured for the probe that during subsequent two-dimensional imaging, a two-dimensional ultrasound image can coincide as much as possible with a cross section in the length direction of the tissue to be subjected to intervention, thereby ensuring that the interventional object falls within the plane of the ultrasound image as much as possible and thus is completely imaged (since the intervention path of the interventional object is generally planned in the length direction of the tissue to be subjected to intervention). In addition, such configurations can further ensure that a transmitted ultrasonic wave is maintained as perpendicular as possible to the length direction of the interventional object, thereby ensuring higher echo intensity and the effect of imaging the interventional object.

Figure 3:
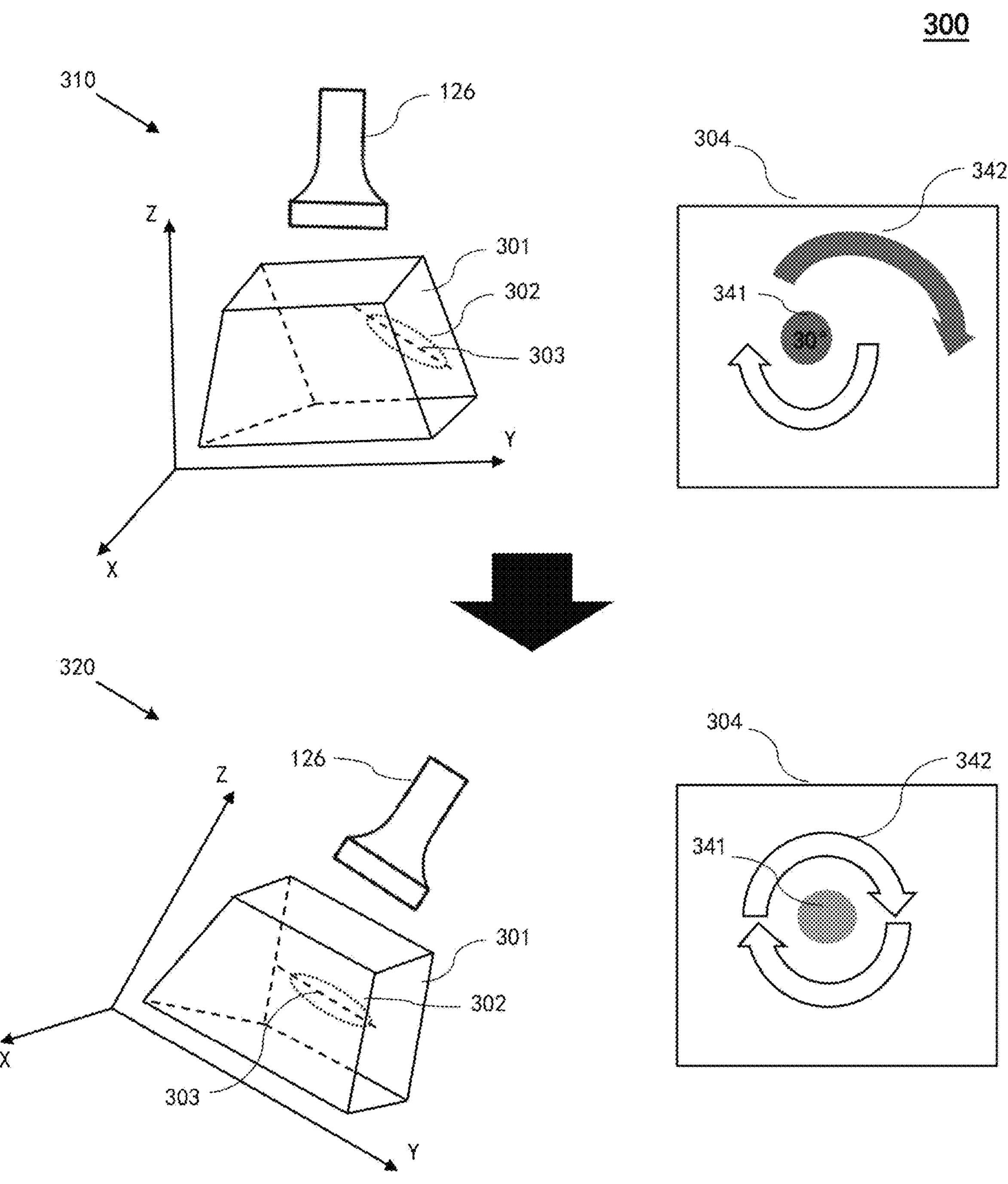
FIG. 3 is a schematic diagram of performing movement guiding for a probe in some embodiments of the present application.

In other words, the above-described movement guide may be understood as guiding the probe to move so as to move the range of the field of view of the volumetric ultrasound image so that the tissue to be subjected to intervention is properly positioned in the volumetric ultrasound image. A detailed description is provided below with reference to FIG. 3. Referring to FIG. 3, FIG. 3 shows a schematic diagram 300 of performing movement guiding for a probe in some embodiments of the present application.

First, please refer to a schematic diagram 310 in which the movement guiding for the probe 126 has not been completed. The probe 126 has a 4D imaging function, and can acquire volumetric data (or a volumetric image) 301 of a tissue to be imaged (not shown). For case of description of parameters of the volumetric ultrasound image in three-dimensional directions, it is common in the art to use the depth direction of the probe as the axial direction thereof, such as a Z-axis direction shown in FIG. 3. The plane parallel to a surface wafer of the probe is referred to as a lateral plane, such as the plane in which the X-Y axis shown in FIG. 3 is located. Furthermore, in a mechanical 4D probe, the X axis and the Y axis may also respectively represent a pitch direction and a scan direction. The scan direction may be understood as a direction in which the wafer in the mechanical 4D probe is driven to perform a scan, and the pitch direction may be understood as a direction perpendicular to the scan direction. It can be understood that the definitions of the directions of an E4D probe are similar to those of the mechanical 4D probe.

As shown in 310, the method described in the embodiments of the present application can use the probe 126 to acquire a volumetric ultrasound image covering a large range of a tissue to be imaged, so as to quickly and accurately identify a tissue to be subjected to intervention 302 (e.g., a tumor) therein. As set forth above in the present application, the processor can identify the tissue to be subjected to intervention 302 by means of an image recognition algorithm, and can acquire other image information. In a non-limiting embodiment, the image information may include size information of the tissue to be subjected to intervention 302, for example, the size of an outer contour thereof. Accordingly, the length direction 303 of the tissue to be subjected to intervention 302 can also be determined. On that basis, the processor can generate a movement guide 304 for the probe 126, and display the same (the display is not shown). Such configurations can ensure that the physician quickly perceives a site to be subjected to intervention in the field of view, and can also ensure that the physician is assisted in efficiently adjusting the position of the probe and the like to achieve an optimal imaging effect.

In a non-limiting embodiment, the movement guide 304 may include at least one of a rotational guide for the probe and a translational guide for the probe along a surface of the tissue to be imaged. As shown in FIG. 3, the movement guide 304 may include a rotational guide 341 for the probe 126 and a translational guide 342 for the probe 126 along a surface (not shown in the figure) of the tissue to be imaged. In the example shown in FIG. 3, the rotational guide 341 directly indicates an angle (e.g., 30°) by which the probe needs to be rotated. The translational guide 342 provides a direction in which the probe needs be translated. In a preferred example, the translational guide 342 may further provide a distance by which the probe needs to be translated. For example, the distance to the end of an arrow relative to the rotational guide 341 (also used to indicate the current position of the probe) may be understood as a distance by which the probe needs to move. The direction of the arrow may also be used to indicate the direction in which the probe needs to rotate, e.g., clockwise or counterclockwise. In addition, in order to more clearly prompt the physician, the rotational guide 341 and the translational guide 342, when present, may also be represented in a first color, e.g., red. In this way, the physician can intuitively learn a movement operation to be performed. It should be noted that the movement guide 304 shown in FIG. 3 is only a preferred embodiment of the present application, but no exclusive limitation is made.

Continue to refer to refer to a schematic diagram 320 in which the movement guiding for the probe 126 has been completed. After the physician positions the probe 126 in a suitable position according to the movement guide 304, a display status of the movement guide 304 perceptibly changes. For example, the rotational guide 341 and the translational guide 342 no longer provide a guide. In other words, the movement guide 304 may also include an indication of whether the probe has reached a predetermined movement position. In a preferred example, the above-described guide may also be changed to be displayed in a second color, e.g., green. The physician can quickly understand whether the rotation operation or the translation operation has been completed.

As shown in 320 of FIG. 300, after the probe 126 is operated, the field of view thereof changes, and the obtained volumetric data or volumetric image 301 undergoes a perceptible change in orientation compared to 310. It can be seen that the tissue to be subjected to intervention 302 in this case is substantially located in the middle position of the volumetric image 301. Furthermore, it is also possible to cause the length direction 303 of the tissue to be subjected to intervention 302 to be substantially parallel to the lateral plane (the X-Y plane) of the volumetric image. Although the volumetric image 301 shown in FIG. 300 is tilted, it can be understood that when reflected in a screen on the display apparatus of the ultrasound imaging system, what a user can perceive is a change in the position and orientation of the tissue to be subjected to intervention 302 in the image. It can be understood that substantially located in the middle position and substantially parallel to the lateral plane mean that a certain error within a reasonable range is allowed. Furthermore, in some cases, in consideration of various factors such as the surface of the tissue to be imaged, the orientation of the tissue to be subjected to intervention 302, etc., it may be difficult to cause the lateral plane to be parallel to the length direction of the tissue to be subjected to intervention, and the deviation resulting from the above factors does not depart from the spirit of the present application.

Furthermore, it can be understood that although FIG. 3 only shows the probe movement guide 304 before movement of the probe 126 (FIG. 310) and after movement of the probe 126 (FIG. 320), the movement guide 304 may change dynamically according to the real-time volumetric image 301 and the tissue to be subjected to intervention 302 during real-time movement of the probe 126. Specifically, the processor may perform, during movement of the probe 126, real-time volumetric imaging on the tissue to be imaged, and generate and display, in real time, the movement guide 304 for the probe 126 during movement of the probe 126. Such configurations can enable the movement guide 304 to be more prompt and more accurate and to fit an actual ultrasonic scanning procedure. The physician can focus more on the more intuitive movement guide 304 during movement and adjustment of the probe, thereby improving the efficiency of probe adjustment.

Figure 4:
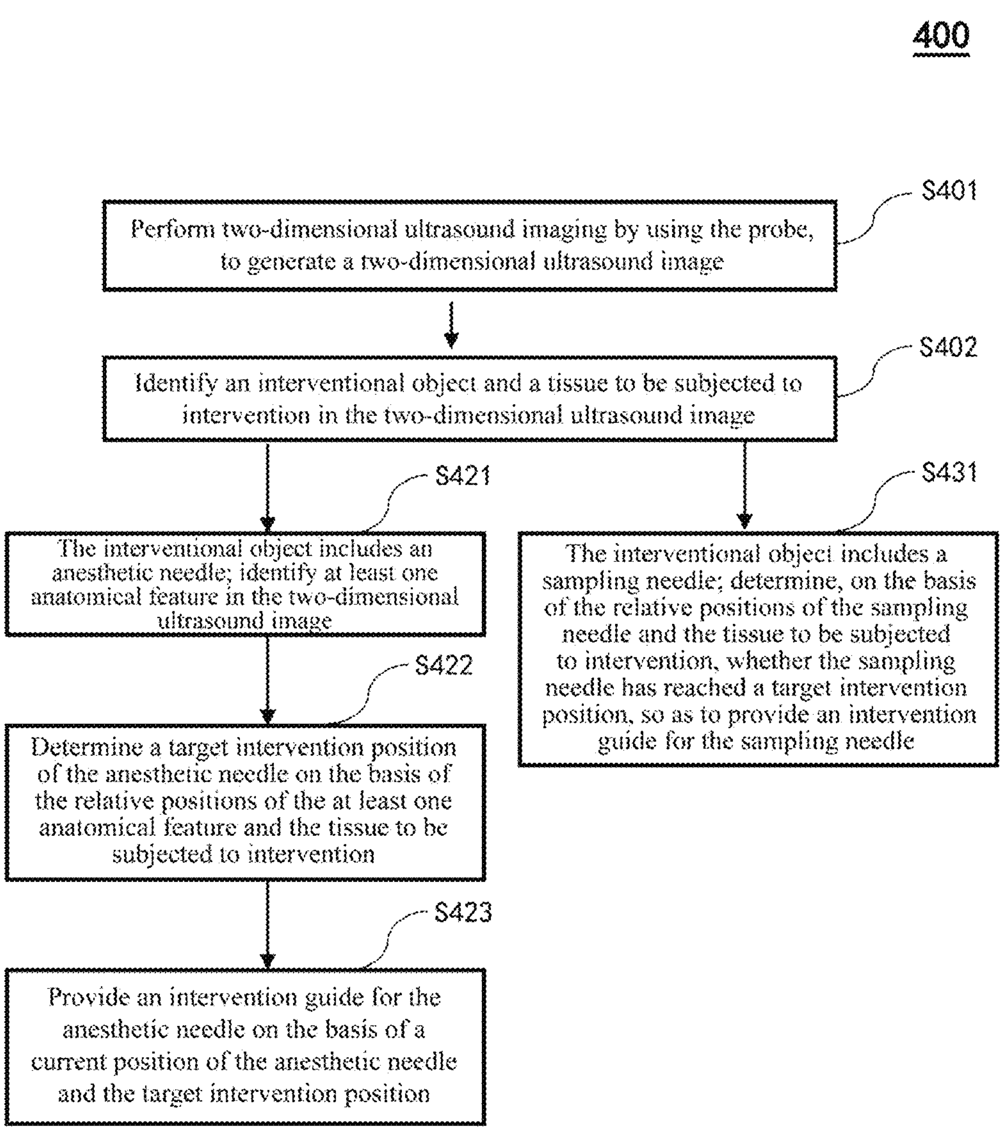
FIG. 4 is a schematic diagram of an ultrasound imaging method in some other embodiments of the present application.

Further, the inventors have recognized that a complete interventional operation typically further includes anesthesia and/or sampling (including a biopsy or lesion removal). In view of this, improvements to the accuracy and efficiency of the interventional procedure are provided in some embodiments of the present application. Referring to FIG. 4, FIG. 4 shows a schematic diagram of an ultrasound imaging method 400 according to some other embodiments of the present application.

In step 401, two-dimensional ultrasound imaging is performed by using the probe, to generate a two-dimensional ultrasound image. The procedure can be implemented by the processor set forth in any one of the above embodiments. In some embodiments, the two-dimensional ultrasound imaging may be performed by the processor by controlling a 4D probe in a two-dimensional mode. The movement guiding performed for the 4D probe by using the embodiments disclosed in the present application has been described in detail above. After the movement guiding, the 4D probe can be aligned with an interventional object even in a two-dimensional imaging mode, thereby ensuring that the interventional object is exposed in the field of view. In another embodiment, the two-dimensional ultrasound imaging may be performed by the processor by controlling the 4D probe to acquire volumetric ultrasound data and selecting an appropriate ultrasound section therefrom to generate the two-dimensional ultrasound image. It can be understood that in such a mode, the movement guide set forth in any of the above embodiments can also ensure that the two-dimensional ultrasound section including the interventional object has a good imaging effect.

In step 402, an interventional object and tissue to be subjected to intervention are identified in the two-dimensional ultrasound image. An image recognition method used by the processor for the interventional object and the tissue to be subjected to intervention has been described in detail above and will not be repeated herein.

In the above embodiment, volumetric ultrasound imaging is used in a probe position adjustment stage prior to an interventional procedure, and the probe is further used during the interventional procedure to perform two-dimensional ultrasound imaging to provide an intuitive and clear image of the interventional object, thereby in one aspect, quickly and accurately locating the probe position, and in another aspect, providing clear image information for intervention.

Optionally, the ultrasound imaging method 400 of the present application may further include additional steps described below. Specific details and technical effects of these steps are described in detail below.

In some optional embodiments, according to different categories of interventional object, the ultrasound imaging method 400 may further include steps 421 to 423, or the ultrasound imaging method 400 may further include step 431. Steps 421 to 423 may be selected when the interventional object includes an anesthetic needle. Step 431 may be selected when the interventional object includes an interventional needle. In some examples, steps 421 to 423 and step 431 may be included in a complete workflow.

When the interventional object includes an anesthetic needle, steps 421 to 423 may be performed.

Figure 5:
FIG. 5 is a schematic diagram of performing two-dimensional ultrasound imaging on an interventional object according to some embodiments of the present application.
Figure 5:
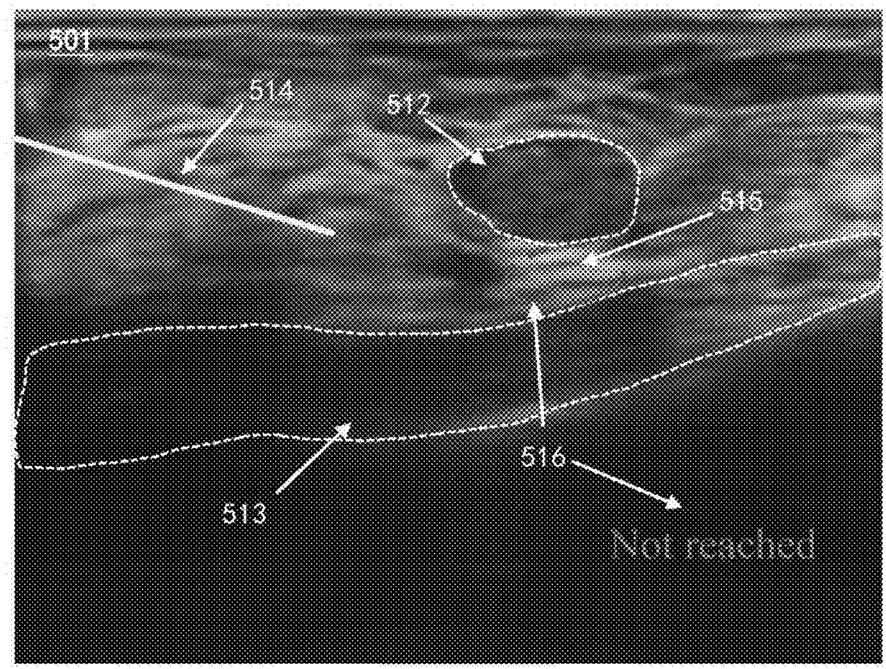
Figure 5:
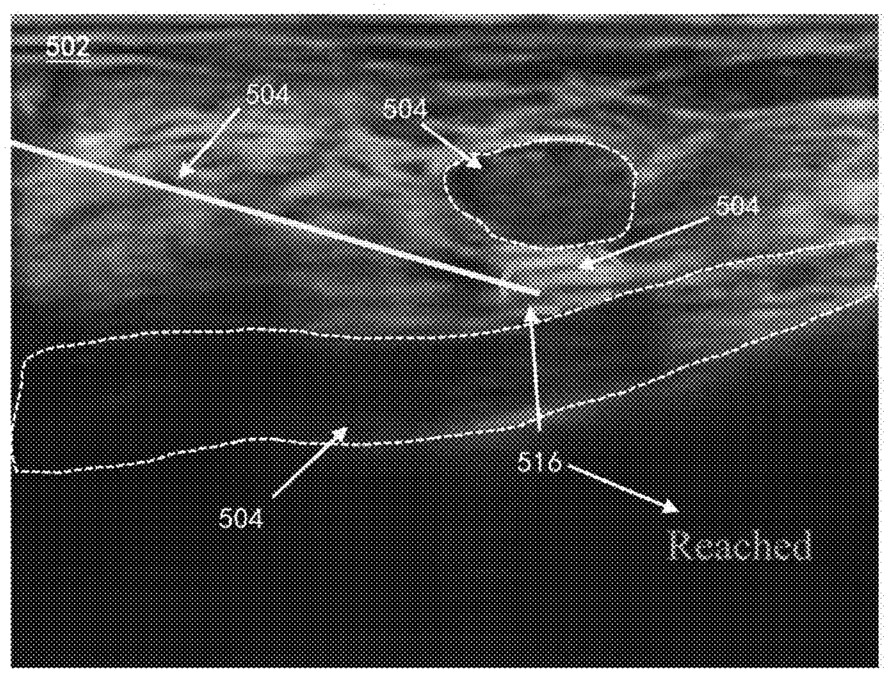

In step 421, at least one anatomical feature is identified in the two-dimensional ultrasound image. The image recognition method is as described in any one of the above embodiments, and will not be further described. The anatomical feature may be a critical position inside a tissue to be imaged. An exemplary description is provided below by using a breast as an example. Referring to FIG. 5, FIG. 5 shows a schematic diagram 500 of performing two-dimensional ultrasound imaging on an interventional object according to some embodiments of the present application. A two-dimensional image 501 of the tissue to be imaged includes a tissue to be subjected to intervention 512 (a tumor) and an anatomical feature 513. The anatomical feature 513 may vary depending on the tissue to be imaged. The anatomical feature 513 shown in FIG. 5 may be the pectoralis major. It can be understood that in other embodiments, there may be one or a plurality of anatomical features. In addition, the two-dimensional image 501 further includes an interventional object, i.e., an anesthetic needle 514.

Further, in step 422, a target intervention position of the anesthetic needle is determined on the basis of the relative positions of the at least one anatomical feature and the tissue to be subjected to intervention. The determination process described above may be performed automatically by the processor. The embodiments of the present application reduce the workflow of the physician and improve work efficiency compared to conventional planning of an intervention path. With continued reference to the two-dimensional image 501, the target intervention position 515 may be determined according to the positional relationship between the anatomical feature 513 and the tissue to be subjected to intervention 512. For example, the target intervention position 515 may be located between the anatomical feature 513 and the tissue to be subjected to intervention 512, thereby in one aspect, ensuring an anesthetic effect, and in another aspect, not having an excessive effect on the tissue structures of the anatomical feature 513 and the tissue to be subjected to intervention 512.

In step 423, an intervention guide for the anesthetic needle is provided on the basis of a current position of the anesthetic needle and the target intervention position. Such a configuration can improve the work efficiency of the physician and reduce the amount of manual work. The intervention guide may be visually displayed on the display apparatus. An exemplary description is provided with reference to FIG. 5. Referring to both the two-dimensional image 501 and a two-dimensional image 502, the two-dimensional image 501 and a two-dimensional image 502 respectively represent different representations of the intervention guide 516 before the interventional object 514 reaches the target position when the interventional object 514 reaches the target position. In the two-dimensional image 501, the interventional object 514 at this time has not yet reached the target intervention position 515. In this case, the intervention guide 516 may include, in one aspect, a text prompt of "not reached" and may also include, in another aspect, a first color prompt of the border of the target intervention position 515, e.g., red. The physician can visually observe the progress of the intervention from the image. Further, in the two-dimensional image 502, the interventional object 514 at this time has reached the target intervention position 515. In this case, the intervention guide 516 may include, in one aspect, a text prompt of "reached" and may also include, in another aspect, a second color prompt of the border of the target intervention position 515, e.g., green. It should be noted that the above visual representation of the intervention guide is a preferred embodiment of the present application, but no exclusive limitation is made.

When the interventional object includes a sampling needle, step 431 may be performed. It should be noted that the sampling needle may be any sampling needle in the art, and may be selected according to various factors such as usage habits of the physician, the tissue to be subjected to intervention, and the site to be subjected to intervention, etc. The present disclosure is not limited. In addition, sampling is useful for a variety of purposes including, for example, extraction of a small sample in an object to be subjected to intervention for purposes such as a biopsy, and complete removal of an object to be subjected to intervention.

In step 431, it is determined, on the basis of the relative positions of the sampling needle and the tissue to be subjected to intervention, whether the sampling needle has reached a target intervention position, so as to provide an intervention guide for the sampling needle. This step may be performed with reference to step 423 and the description of the corresponding embodiment in FIG. 5, a main difference being that the target intervention position of the sampling needle is a position at which the sampling needle is close to or contacts the tissue to be subjected to intervention. Whether the sampling needle has reached the target intervention position is determined mainly on the basis of the relative positions of the sampling needle and the tissue to be subjected to intervention.

It can be understood that identification of the category of the sampling needle described above may be based on user input. For example, a specific imaging category may be selected by the physician as to whether imaging is for an anesthetic needle or a sampling needle. Alternatively, the identification of the sampling needle may be automatically performed by the processor, e.g., automatically determined according to the morphology of the sampling needle in the image.

In addition to performing guiding in the process of the interventional object reaching the target position, guiding may also be performed in a process of the interventional object being operated after the interventional object reaches the target position in some embodiments of the present application. For example, when the interventional object is a sampling needle, real-time auxiliary imaging may also be performed in a sampling procedure of the sampling needle in some embodiments of the present application. Specifically, the two-dimensional ultrasound image may include a first image and a second image, the length direction of the sampling needle passing through the plane in which the first image is located and being perpendicular to the plane in which the second image is located.

Such configurations enable image information of the sampling needle in two dimensions to be provided simultaneously. The first image can provide information of the sampling needle in the length direction, i.e., the longitudinal direction, thereby ensuring that a sampling port can be positioned at the position of tissue to be subjected to intervention, e.g., a tumor. The second image can provide information of a direction perpendicular to the length direction of the sampling needle, i.e., a transverse direction, thereby ensuring that the sampling needle does not deviate from the tissue to be subjected to intervention. Such configurations are not possible with the use of a two-dimensional probe in conventional interventional operations. This is because a two-dimensional probe can typically acquire image information of only one section. In the present application, the 4D probe is used to perform imaging in a sampling process, so that a plurality of two-dimensional images of different sections can be acquired according to requirements, thereby providing valuable multi-dimensional image information.

Figure 6:
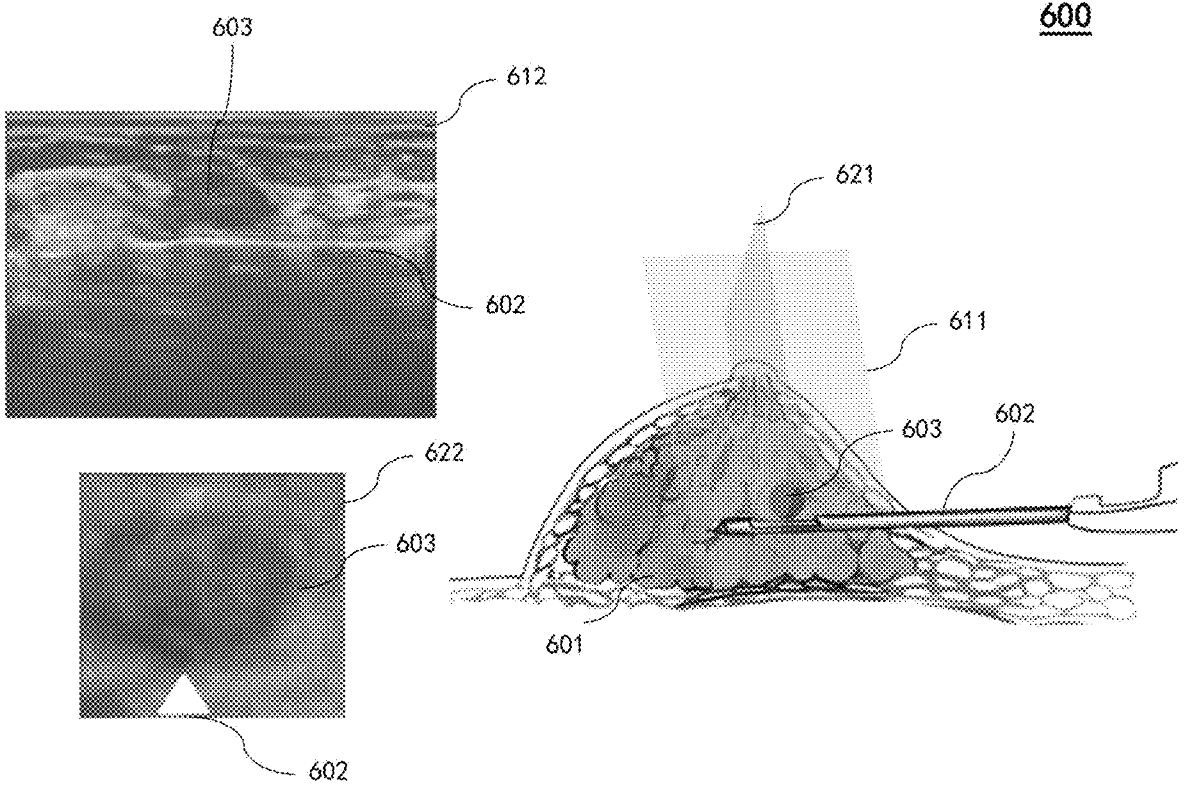
FIG. 6 is a schematic diagram of imaging a sampling needle in some embodiments of the present application.

To illustrate the above solution more clearly, reference is made to FIG. 6. FIG. 6 shows a schematic diagram 600 of imaging a sampling needle in some embodiments of the present application.

As shown in FIG. 600, illustration is provided by using a breast 601 as an example of a tissue to be imaged. After a sampling needle 602 reaches a tissue to be sampled 603, a probe (not shown) can perform imaging from two planes, i.e., a first plane 611 and a second plane 621. The first plane 611 includes the sampling needle 602, and the second plane 621 is perpendicular to the sampling needle 602.

Further, by means of ultrasound imaging, a first image 612 of the first plane 611 and a second image 622 of the second plane 621 may be generated, respectively. In the first image 612, extension of the sampling needle 602 in the length direction, particularly a positional relationship with the tissue to be sampled 603 in the length direction, can be clearly observed. In the second image 622, information of the sampling needle 602 in the cross-sectional direction can be clearly observed, and in comparison with the first image 612, the second image 622 can additionally provide image information about whether the sampling needle 602 transversely deviates from the tissue to be sampled 603. In summary, the image information of two dimensions can ensure that the physician performs efficient and accurate sampling.

Some embodiments of the present application further provide an ultrasound imaging system, which may be as shown in FIG. 1 or any other one. The system includes: a probe; a processor, configured to perform the method set forth in any of the above embodiments of the present application; and a display apparatus, used to receive a signal from the processor and perform a display operation.

Some embodiments of the present application further provide a non-transitory computer-readable medium, where the non-transitory computer-readable medium has a computer program stored thereon, the computer program has at least one code segment, and the at least one code segment is executable by a machine so as to enable the machine to execute the steps of the method in any of the above embodiments.

Correspondingly, the present disclosure may be implemented by means of hardware, software, or a combination of hardware and software. The present disclosure may be implemented in at least one computer system in a centralized manner, or implemented in a distributed manner; and in the distributed manner, different elements are distributed on a plurality of interconnected computer systems. Any type of computer system or other apparatus suitable for implementing the methods described herein is considered to be appropriate.

Various embodiments may also be embedded in a computer program product, which includes all features capable of implementing the methods described herein, and the computer program product is capable of executing these methods when loaded into a computer system. The computer program in this context means any expression in any language, code, or symbol of an instruction set intended to enable a system having information processing capabilities to execute a specific function directly or after any or both of the following: a) conversion to another language, code, or symbol; and b) replication in different material forms.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:

1. An ultrasound imaging system to support guiding an interventional object, comprising:

a probe;

a display apparatus;

a processor configured to:

control the probe to obtain an ultrasonic echo signal from a tissue to be imaged;

process the ultrasonic echo signal, in real time, to generate a volumetric ultrasound image of the tissue to be imaged;

identify, in the volumetric image, a tissue to be subjected to intervention and determine a length direction of the tissue to be subject to intervention, the length direction being a direction of the greatest length of the tissue to be subject to intervention and generate, a movement guide for the probe having a rotational guide and a translational guide that substantially center the tissue to be subject to intervention within the volumetric image and align the length direction substantially parallel to a lateral plane of the volumetric image;

based on movement of the probe, updating, in real time, the movement guide to substantially center the tissue to be subject to intervention within the volumetric image and align the length direction substantially parallel to a lateral plane of the volumetric image; and control the display apparatus to display the movement guide.

2. The system according to claim 1, wherein the image information of the tissue to be subjected to intervention comprises:

size information of the tissue to be subjected to intervention, and/or orientation information of the tissue to be subjected to intervention in the volumetric ultrasound image.

3. The system according to claim 1, wherein the movement guide comprises at least one of a rotational guide for the probe, a translational guide for the probe along a surface of the tissue to be imaged, and an indication of whether the probe has reached a predetermined movement position.

4. The system according to claim 1, wherein the processor is further configured to:

perform, during movement of the probe, real-time volumetric imaging on the tissue to be imaged; and generate and display, in real time, the movement guide for the probe during movement of the probe.

5. The system according to claim 1, wherein the processor is further configured to:

perform two-dimensional ultrasound imaging by using the probe, to generate a two-dimensional ultrasound image; and identify an interventional object and the tissue to be subjected to intervention in the two-dimensional ultrasound image.

6. The system according to claim 5, wherein the interventional object comprises an anesthetic needle, and wherein the processor is further configured to:

identify at least one anatomical feature in the two-dimensional ultrasound image;

determine a target intervention position of the anesthetic needle based on relative positions of the at least one anatomical feature and the tissue to be subjected to intervention; and provide an intervention guide for the anesthetic needle based on a current position of the anesthetic needle and the target intervention position.

7. The system according to claim 5, wherein the interventional object comprises a sampling needle, and wherein the processor is further configured to:

determine, based on relative positions of the sampling needle and the tissue to be subjected to intervention, whether the sampling needle has reached a target intervention position, to provide an intervention guide for the sampling needle.

8. The system according to claim 5, wherein the interventional object comprises a sampling needle, and the two-dimensional ultrasound image comprises a first image and a second image, a length direction of the sampling needle passing through the plane in which the first image is located and being perpendicular to the plane in which the second image is located.

9. An ultrasound imaging method to support guiding an interventional object, comprising:

receiving, by using a probe, an ultrasonic echo signal from a tissue to be imaged;

processing the ultrasonic echo signal to generate, in real time, a volumetric ultrasound image of the tissue to be imaged;

identifying, in the volumetric image, a tissue to be subjected to intervention and determining a length direction of the tissue to be subject to intervention, the length direction being a direction of the greatest length of the tissue to be subject to intervention;

generating and displaying, a movement guide for the probe having a rotational guide and a translational guide that substantially center the tissue to be subject to intervention within the volumetric image and align the length direction substantially parallel to a lateral plane of the volumetric image; and based on movement of the probe, updating, in real time, the movement guide to substantially center the tissue to be subject to intervention within the volumetric image and align the length direction substantially parallel to a lateral plane of the volumetric image.

10. The method according to claim 9, wherein the image information of the tissue to be subjected to intervention comprises:

size information of the tissue to be subjected to intervention, and/or orientation information of the tissue to be subjected to intervention in the volumetric ultrasound image.

11. The method according to claim 9, wherein the movement guide comprises an indication of whether the probe has reached a predetermined movement position.

12. The method according to claim 9, further comprising:

performing, during movement of the probe, real-time volumetric imaging on the tissue to be imaged; and generating and displaying, in real time, the movement guide for the probe during movement of the probe.

13. The method according to claim 9, further comprising:

performing two-dimensional ultrasound imaging by using the probe, to generate a two-dimensional ultrasound image; and identifying an interventional object and the tissue to be subjected to intervention in the two-dimensional ultrasound image.

14. The method according to claim 13, wherein the interventional object comprises an anesthetic needle, and the method further comprises:

identifying at least one anatomical feature in the two-dimensional ultrasound image;

determining a target intervention position of the anesthetic needle based on relative positions of the at least one anatomical feature and the tissue to be subjected to intervention; and providing an intervention guide for the anesthetic needle based on a current position of the anesthetic needle and the target intervention position.

15. The method according to claim 13, wherein the interventional object comprises a sampling needle, and the method further comprises:

determining, based on relative positions of the sampling needle and the tissue to be subjected to intervention, whether the sampling needle has reached a target intervention position, to provide an intervention guide for the sampling needle.

16. The method according to claim 13, wherein the interventional object comprises a sampling needle, and the two-dimensional ultrasound image comprises a first image and a second image, a length direction of the sampling needle passing through the plane in which the first image is located and being perpendicular to the plane in which the second image is located.

17. A non-transitory computer-readable medium, the non-transitory computer-readable medium having a computer program stored thereon, the computer program having at least one code segment, and the at least one code segment being executable by a machine to enable the machine to execute the steps of:

obtaining an ultrasonic echo signal from a tissue to be imaged;

processing the ultrasonic echo signal to generate, in real time, a volumetric ultrasound image of the tissue to be imaged;

identifying, in the volumetric image, a tissue to be subjected to intervention and determining a length direction of the tissue to be subject to intervention, the length direction being a direction of the greatest length of the tissue to be subject to intervention; and generating and displaying a movement guide for the probe having a rotational guide and a translational guide that substantially center the tissue to be subject to intervention within the volumetric image and align the length direction substantially parallel to a lateral plane of the volumetric image; and based on movement of a probe, updating, in real time, the movement guide to substantially center the tissue to be subject to intervention within the volumetric image and align the length direction substantially parallel to a lateral plane of the volumetric image.

* * * * *